United States Patent
Mashburn et al.

(10) Patent No.: US 6,886,764 B2
(45) Date of Patent: May 3, 2005

(54) DEVICE AND PROCESS FOR PULVERIZING SOLID MATERIALS

(75) Inventors: William Mashburn, Raleigh, NC (US); Lisa DeVane, Elizabethtown, NC (US); Frederick Jaeger, Apex, NC (US); Norman Glassbrook, Chapel Hill, NC (US)

(73) Assignee: Icoria, Inc., Research Triangle Park, NC (US)

( * ) Notice: Subject to any disclaimer, the term of this patent is extended or adjusted under 35 U.S.C. 154(b) by 153 days.

(21) Appl. No.: 09/870,191

(22) Filed: May 30, 2001

(65) Prior Publication Data

US 2003/0025018 A1 Feb. 6, 2003

(51) Int. Cl.⁷ ............................................... B02C 19/00
(52) U.S. Cl. ........................................... 241/175; 241/2
(58) Field of Search ............................... 241/30, 175, 2

(56) References Cited

U.S. PATENT DOCUMENTS

| | | | | |
|---|---|---|---|---|
| 2,247,978 A | * | 7/1941 | Van Arkel | 366/110 |
| 4,295,613 A | * | 10/1981 | Moore et al. | 241/2 |
| 5,464,773 A | * | 11/1995 | Melendez et al. | 435/306.1 |
| 5,707,861 A | * | 1/1998 | Sherman et al. | 435/306.1 |
| 5,921,477 A | * | 7/1999 | Tomes et al. | 241/2 |
| 6,235,501 B1 | * | 5/2001 | Gautsch et al. | 435/91.1 |

* cited by examiner

*Primary Examiner*—Mark Rosenbaum
(74) *Attorney, Agent, or Firm*—Timothy G. Hofmeyer; Eric J. Kron; Laura L. Kiefer

(57) ABSTRACT

A device and process for pulverizing solid materials is provided, which generates vertical and horizontal motion of grinding beads in multiple tube samples containing a sample to be pulverized.

24 Claims, 6 Drawing Sheets

DEVICE AND PROCESS FOR PULVERIZING SOLID MATERIALS

FIELD OF THE INVENTION

The present invention relates generally to a device and process for pulverizing solid materials. In particular, the device and process provide vertical and horizontal motion to grinding beads in multiple sample containers, each containing an individual sample to be pulverized.

BACKGROUND

In the field of high through-put biochemical profiling it is important that a large number of samples be processed in a uniform and reproducible manner. In particular, it has been difficult to achieve a satisfactory level of uniformity in the initial processing of solid materials. Such initial processing generally involves grinding or pulverizing starting material to create a large amount of surface area, thereby increasing the efficiency of subsequent treatments, such as extraction. Materials that are processed include a wide range of friable substances such as seeds, leaves, and other plant materials; solid materials of animal origin; soils; and bulk chemicals or pills.

Existing ball mill devices are currently used for such tasks, but these suffer from several limitations. Perhaps most notably, such devices are limited to only a few samples per single run. Further, the motion cycle is typically somewhat two-dimensional. Therefore, the results provided are limited to uniformity only within a very small number of samples, and the efficiency and uniformity is limited by the single-axis or two-dimensional motion of such devices. Currently, laboratory ball mills are exemplified by products such as the MIKRO-DISMEMBRATOR (B. Braun Biotech, Inc., Allentown, Pa.), which handles a very limited number of sample containers.

Current devices have failed to solve the problem of achieving adequate and uniform motion for simultaneous ball mill pulverization of a relatively large number of samples. Laboratory shaker tables are able to process large numbers of samples, but the motion produced by these tables is much less vigorous than is required to pulverize the samples.

It would be advantageous to have a table-like apparatus that can provide the vigorous motion necessary for thorough and uniform ball mill grinding of a relatively large number of analytical samples. The present invention provides such an apparatus.

SUMMARY

A grinding table capable of processing relatively large numbers of samples in a uniform, thorough, and efficient ball-milling process is disclosed. The grinding table provides uniform processing of a relatively large number of samples at one time, in order to increase reproducibility of subsequent data gathered using samples processed using the device and process described herein.

Accordingly, in one aspect, the grinding table includes a frame comprising vertical and horizontal members; an control unit mounted on the frame; a vibrator in communication with the control unit; a tray mounted on the frame by at least one resilient member, the tray comprising a plurality of sample cells adapted to received a plurality of sample containers including sample material and grinding beads, the tray being in mechanical communication with the vibrator; and a lid for covering and securing the sample containers, where the lid is adapted to be secured to the tray. The grinding table is adapted to generate both horizontal and vertical motion of the grinding beads in the sample containers.

In another aspect, the grinding table includes a frame having vertical and horizontal members; a control unit mounted on the frame; a driver in communication with the control unit; a series of mechanical linkages comprising a counterbalanced cam mechanism in communication with the driver; a tray mounted on the frame via mechanical linkages, where the tray comprises a plurality of sample cells adapted to received a plurality of sample containers containing a sample and grinding beads, and the tray is in mechanical communication with the mechanical linkages which are in communication with the driver; and a lid for covering and securing the sample containers, the lid adapted to be secured to the tray. The grinding table is adapted to generate substantially uniform grinding of the samples by the grinding beads in the sample containers held by the tray.

It is believed that certain aspects of the motion provided to grinding beads within sample containers for the ball-milling process described herein are responsible for the uniform, reproducible and efficient pulverization of a relative large number of samples. Accordingly, in yet another aspect, the invention relates to a process for achieving uniform and reproducible pulverization of friable solids using a ball-mill type action. The process involves securing from about 1 to about 165 sample containers comprising individual samples and grinding beads in a tray, and moving the tray vigorously such that motion of the tray comprises both a horizontal and vertical component.

The grinding table and grinding processes, and various embodiments thereof are described in more detail below. Although the present invention has been described with reference to certain embodiments, other embodiments may achieve similar results and advantages. Variations and modifications of the present invention will be apparent to one skilled in the art and the disclosure herein is intended to cover all such modifications and equivalents.

DETAILED DESCRIPTION

Figure 1:
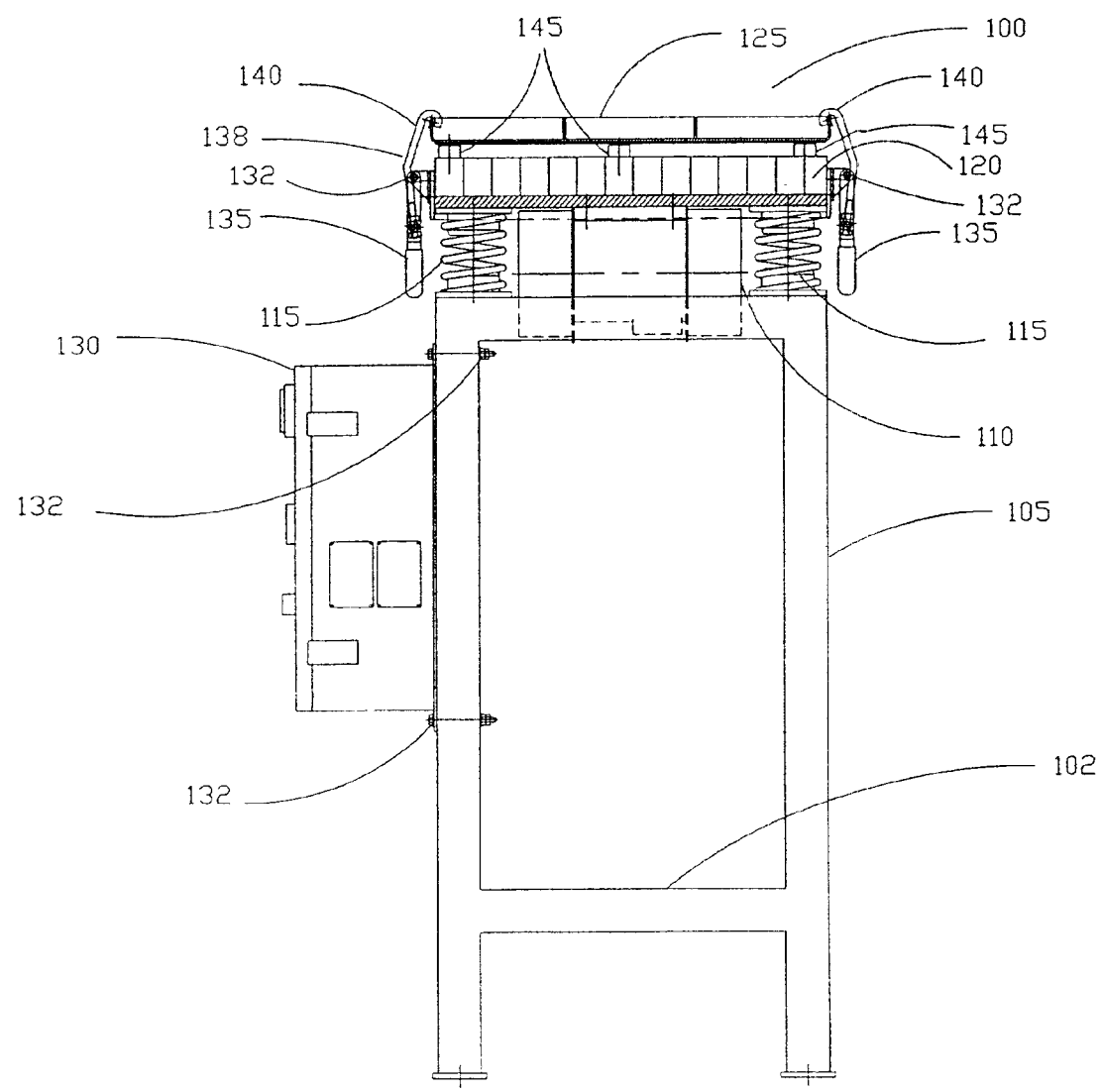
FIG. 1 is a side elevational view of an embodiment of the grinding table described herein.

The grinding table and grinding processes described herein provide a solution to the problem of uniform and reproducible grinding of a relatively large number of samples utilizing a ball mill-type action. Further, the grinding tables provide increased efficiency, uniformity and reproducibility by generating sample motion including both horizontal and vertical components.

Vibrator-Driven Grinding Table

In one aspect, the grinding table includes a frame comprising vertical and horizontal members; an control unit mounted on the frame; a vibrator in communication with the control unit; a tray mounted on the frame by at least one resilient member; and a lid for covering and securing sample containers in the tray. The tray comprises a plurality of sample cells adapted to received sample containers which contain sample material and grinding beads. The tray is in mechanical communication with the vibrator, and the lid is adapted to be secured to the tray. The grinding table is adapted to generate both horizontal and vertical motion of the grinding beads in the sample containers. While not wishing to be bound by a particular theory, the inventors believe that the increased efficiency, uniformity, and reproducibility of results achieved using the grinding tables and processes described herein may be a result of the particular motion provided by the grinding table to the relatively large number of samples processed in a single run.

In one embodiment, the vertical members of the frame are spaced apart to support the horizontal members, and the upper horizontal members form a substantially rectangular top portion. The tray is connected to the frame by a plurality of resilient members, which may be coiled springs.

Also, in one embodiment, the vibrator is a rotary electric vibrator, which may be mounted in contact with a bottom surface of the tray. The electric vibrator may be controlled by an electrical control unit having a start button, a stop button, a speed display, a speed control, a disconnect switch, and/or a process timer.

In one embodiment, the tray further comprises at least one holding means, such as a clamp, adapted to secure the lid to the tray. Generally, a clamp will be provided at an approximate midpoint of each side of a substantially rectangular tray. Each clamp typically comprises a hook portion which is positioned to contact the top portion of a lid, and which is adapted to be locked into place via the downward motion of a handle portion.

One embodiment of the grinding table of the invention is adapted to secure multiple sample containers using from about 1 sample cell to about 165 sample cells. In another embodiment, the grinding table includes at least about 50 sample cells. In still another embodiment, the grinding table includes at least about 150 sample cells. In yet another embodiment, the grinding table includes about 165 sample cells.

Accordingly, the grinding table generally includes a frame which supports a sample tray on resilient members, preferable coiled springs. Typically, a rotary electric vibrator is mounted on the bottom surface of the sample tray. The vibrator is connected to an electrical control panel which allows for starting, stopping, timing runs, and controlling speed. The run time and speed may be displayed on the control panel. Although a variety of vibrators may be used, a preferred model is the INVICTA L SERIES vibrator (available from Hindon Corp., Engineered Products Division, Charleston, S.C.).

Because of the vigorous motion generated for efficient pulverization, the mounting instructions provided by the vibrator manufacturer should be followed carefully. Further, the frame should be of sufficient strength and durability to withstand sustained operation of the grinding table. For example, the frame may include vertical and horizontal members of two inch by two inch steel tube (0.12 inch wall). In addition to a top support portion formed by similar horizontal members, horizontal members may be provided proximal to the bottom of the frame to reinforce the rigidity of the frame. Also, tabs or flanges are provided for bolting the base of the floor at each leg or vertical member of the frame.

The sample tray contains an array of tube cells which are sized to receive sample tubes in close contact with the walls of the tube cells. Generally, at least a portion of the sample container will project above the upper edge (or open top) of the tube cell. Accordingly, the tops of an array of sample containers will project generally above the top surface of the sample tray formed by the open tops of the tube cells. The grinding table provides a lid which contacts the tops of the sample containers and which may be secured to the sample tray via clamps or other suitable holding means. The clamps are typically positioned in a spaced-apart fashion, preferably in approximately the center of each side of the sample tray. The lid may include a padded, non-slip material on its bottom surface that contacts the sample containers. Preferably, this material is a rubber sheet.

When the lid of the grinding table is clamped on the sample tray, the sample containers are securely held in individual tube cells during a grinding run. The sample containers may be made of any suitable material, however, polypropylene is a particularly preferred material for most applications. In addition to sample material, the sample container will contain beads which may be made of a variety of hard, inert materials. Preferably, the beads are made of zirconium oxide or a ceramic material.

In a typical grinding run, grinding beads and sample material to be pulverized are placed in sample containers, preferably with equal amounts and/or ratios of beads and sample material, and the sample containers are placed into the tube cells. Bead size may range from about 0.08–0.12 inches to about 0.5 inches (about 2–3 mm to about 13 mm). Typically, bead size will be from about 0.19 inches to about 0.4 inches (about 5 mm to about 10 mm). Bead shapes include spherical, a banded satellite, or cylindrical. Shapes such as banded satellites and cylinders may provide cutting edges which allow for increased efficiency in grinding tougher materials. Also, more that one size or shape of bead may in included in the sample container for a particular processing run. For example, in addition to equal amounts of sample material per container, each sample container may contain four 0.4 inch (10 mm) beads, ten 0.25 inch (6.4 mm) beads, and ten 0.19 inch (4.8 mm) beads. Beads may comprise any suitable material, i.e. generally a dense, hard material. Tungsten carbide is one such material. Zirconium oxide is a preferred bead material.

After sample material and beads are placed in the sample containers, the lid is then positioned over the array of sample containers, and the lid holding means are engaged to secure the lid to the sample tray. The cycle timer is set for the proper process time, the start button is pushed to provide power to the vibrator motor, and the motor accelerates to the pre-set speed.

During the grinding run, the vibrator motor causes the sample tray to oscillate both horizontally and vertically. The rapid acceleration causes the grinding beads to move vigorously within the sample containers, thereby pulverizing the sample material. The process is set to continue until the pre-set time has elapsed, whereupon the vibrator motor stops. The lid holding means are then released and the sample containers may be removed.

The grinding table described herein can process a wide range of friable materials according to the foregoing process. Samples such as seeds or other plant material, soils, bulk chemicals, or pills may be uniformly processed with high reproducibility. Also, a relative large number of samples can be simultaneously processed, allowing maximum uniformity among samples processed together in a single run. The device processes samples using a minimum number of mechanical parts, and runs safely and efficiently. Parameters that may be adjusted include the speed, bead size, material, and process time. The grinding table does not require continuous operator monitoring.

Figure 2:
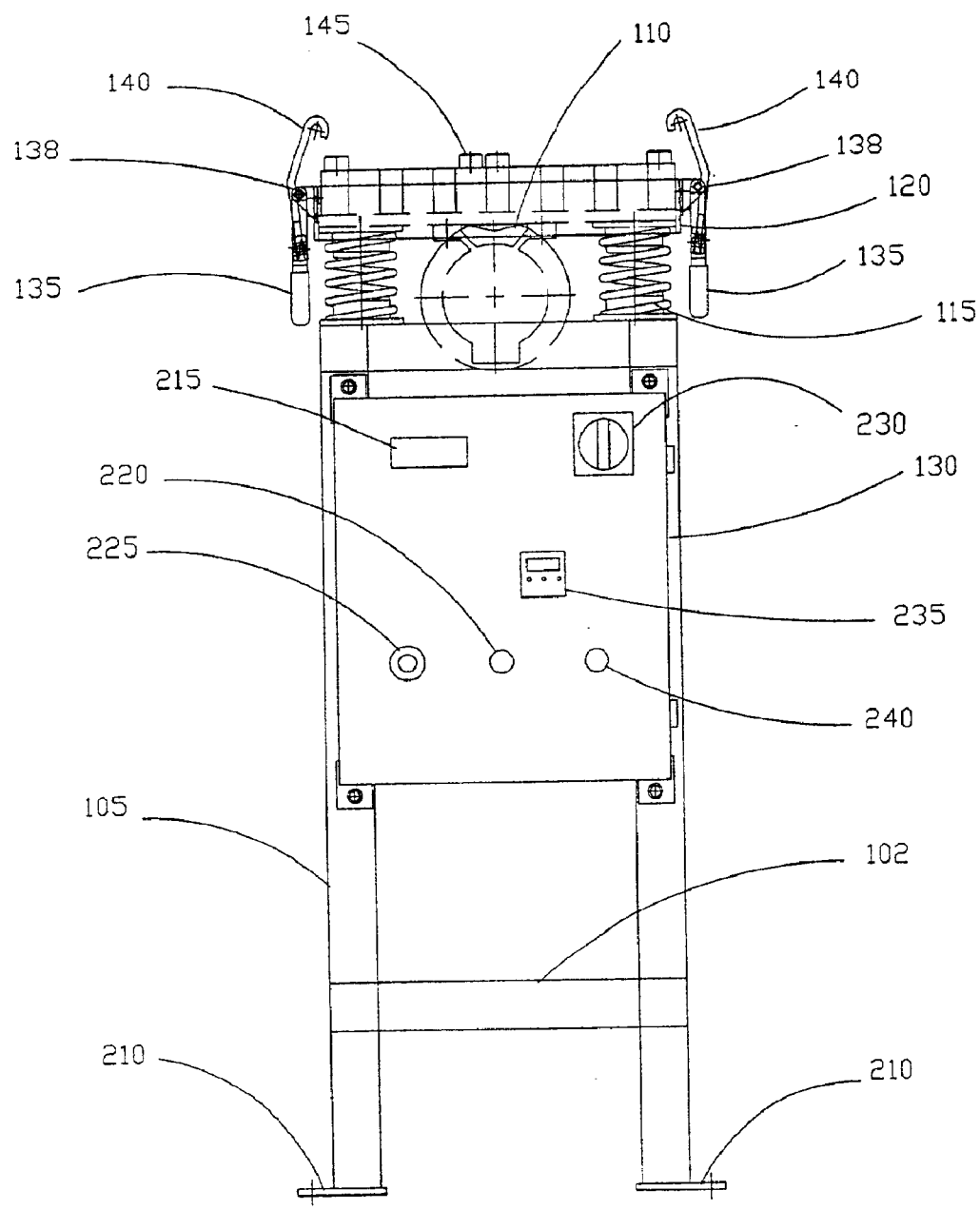
FIG. 2 is a end elevational view of the grinding table, viewed from the right as shown in FIG. 1.

One embodiment of the grinding table described herein is illustrated in FIGS. 1–5. Referring to now to FIG. 1, frame 105 comprising support members 102 supports tray 120 via coiled spring assemblies 115. Rotary vibrator motor 110 is mounted on the bottom surface of tray 120, and is in electrical communication with electrical control panel 130 connected to frame 105 via brackets 132. Clamps 138, comprising top hook portions 140 pivotally connected to lower handle portions 135, are mounted on tray 120 in approximately the center of each side of generally rectangular tray 120 (see FIG. 3). Top hook portions 140 are adapted to contact the top surface of lid 125 and are used to secure lid 125 to tray 120, thereby securing samples containers 145 in tray 120 when handle portion 135 is in the "down" or locked position. In the secured position, lid 125 is actually in contact with the top portion of samples containers 145, such that they are held securely in tray 120 by lid 125. Accordingly, lid 125 further comprises on its bottom surface a sheet of a material which pads and further secures sample containers 145 via contact with the top portion of each container. The bottom surface of lid 125 comprises rubber sheet 400 (see detailed cross-section in FIG. 4), which is particularly well-adapted for this purpose FIG. 2 shows an end view of grinding table 100, as from the right of the view presented in FIG. 1. Lid 125, however, is not shown in FIG. 2. FIG. 2 does show the operational face of electrical control panel 130. Start button 220 and stop button 240 are shown, as is speed control 225 and disconnect switch 230. Process timer 235 and speed display 215 are also shown. FIG. 2 also shows floor mounting flanges 210, which may be important for securing frame 105 due to the vigorous motion of the relatively large and heavy combination of components supported by frame 105.

Figure 3:
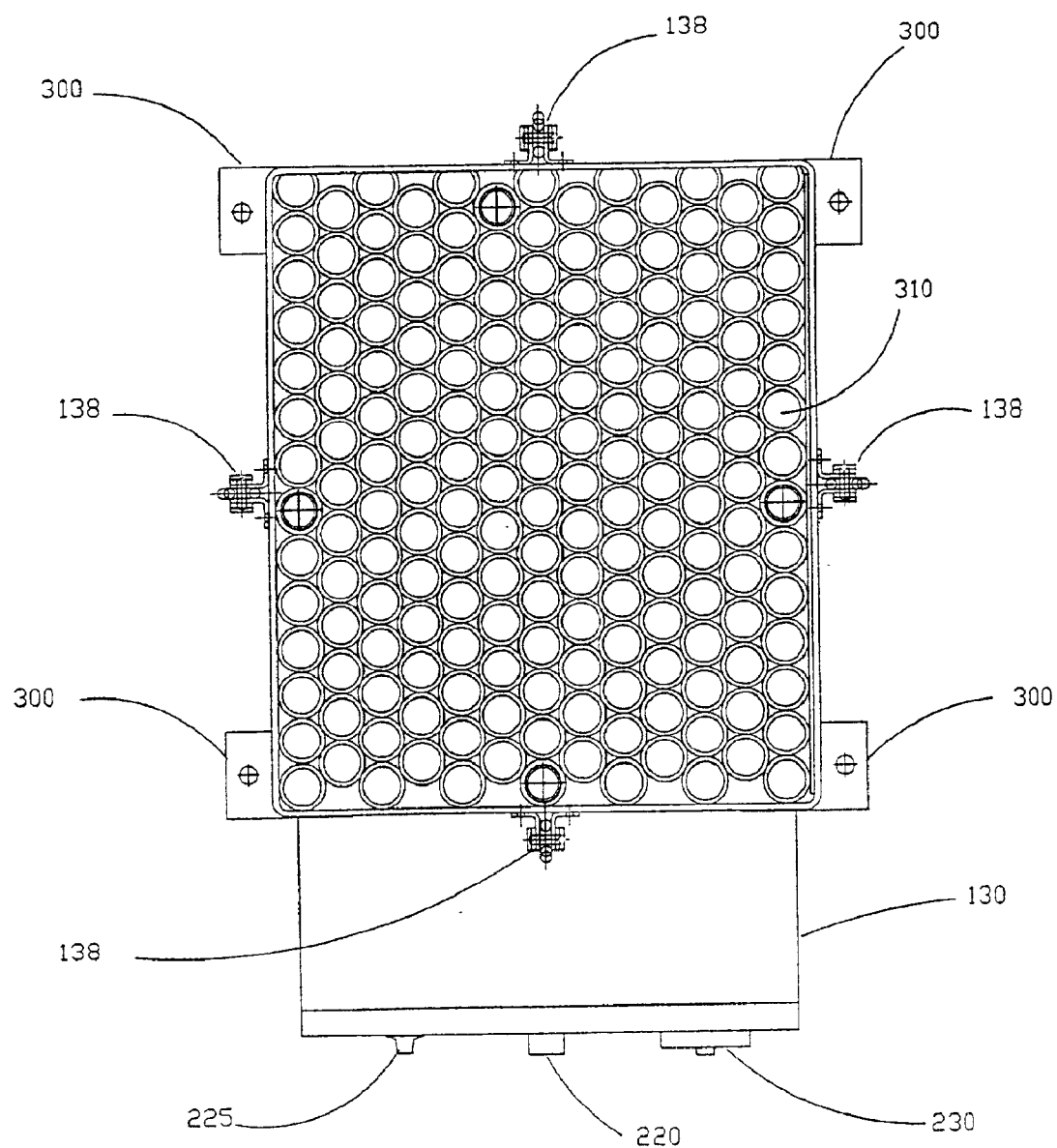
FIG. 3 is an overhead or top view of the grinding table, as shown in FIG. 1.

FIG. 3 shows a top view of grinding table 100, showing the positioning of clamps 138 and the open ends of multiple tube cells 310 arrayed in tray 120. Tray flanges 300 are also shown, which allow tray 120 to be secured to frame 105 via coiled spring assemblies 115.

Figure 4:
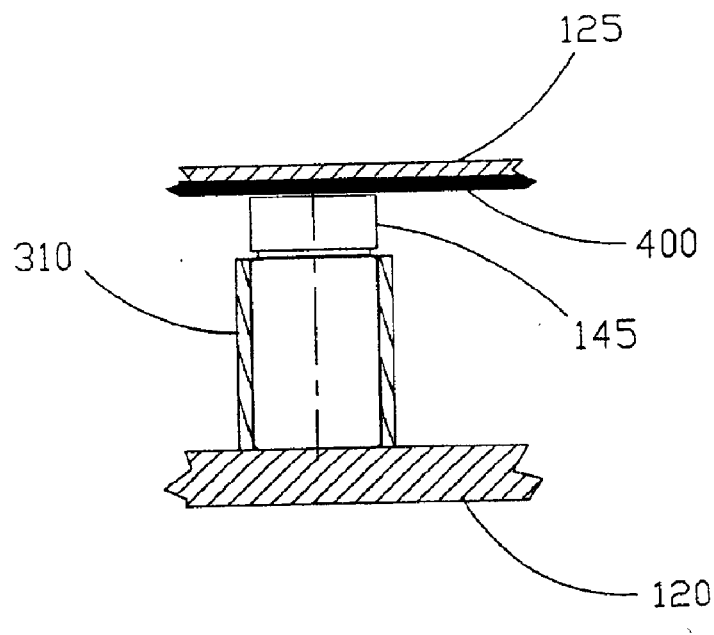
FIG. 4 is a cross-sectional detail of a single sample container and tube cell of the grinding table.

FIG. 4 shown a detailed cross-sectional view of the relationship between lid 125, sample container 145 and tray 120, including individual tube cell 310. When lid 125 is clamped to tray 120 in the secured position, the bottom surface of lid 125 comprising rubber sheet 400 contacts the top of sample container 145 (typically a cap component of container 145) to securely hold container 145 in tube cell 310 during operation of grinding table 100.

Figure 5:
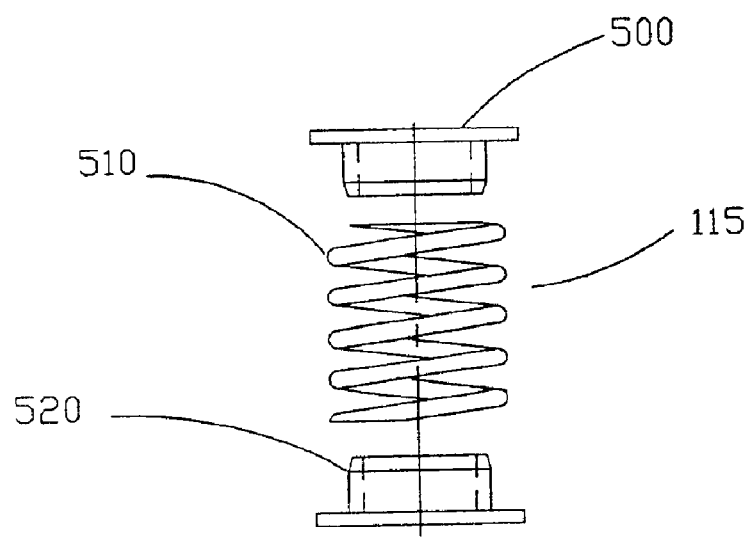
FIG. 5 is an exploded view of a spring assembly of the grinding table.

FIG. 5 shows a detailed view of a coiled spring assembly 115 used to connect tray 120 to frame 105 in one embodiment of the invention. Coiled spring assembly 115 comprises upper projection 500 which is received in the open end of a top portion of coiled spring 510, and corresponding lower projection 520, which is received in the open end of the bottom portion of coiled spring 510.

Mechanical Linkage Grinding Table

In another aspect, the grinding table provides a grinding table includes a driver and mechanical linkages to provide the sample motion necessary for ball mill-type grinding, rather than using a vibrator and resilient members as in the foregoing aspect of the invention.

A grinding table for pulverizing solid materials is provided which comprises a frame having vertical and horizontal members; a control unit mounted on the frame; a driver in communication with the control unit; a series of mechanical linkages comprising a counterbalanced cam mechanism in communication with the driver; a tray mounted on the frame via mechanical linkages, the tray having a plurality of sample cells adapted to received a plurality of sample containers containing a sample and grinding beads, the tray being in mechanical communication with the mechanical linkages which are in communication with the driver; and a lid for covering and securing the sample containers. The lid is adapted to be secured to the tray. The grinding table is adapted to generate substantially uniform grinding of the samples by the grinding beads in the sample containers held by the tray. The series of mechanical linkages in communication with the driver and the mechanical linkages mounting the tray to the frame are also adapted to provide motion to the tray having both a horizontal and vertical component.

The mechanical linkages may comprise pillow block bearing assemblies mounted in corresponding positions on a bottom surface of the tray and on a top portion of the frame. Each corresponding pair of pillow block bearing assemblies is connected by at least one bearing connecting link.

The driver is typically an electric motor mounted to the frame. Generally, the electric motor comprises a drive shaft which communicates with an end cam follower and an associated bearing assembly linked to a connector rod. The connector rod is, in turn, connected at an opposite end to a pillow block bearing assembly mounted on a bottom surface of the tray. In order to stabilize the table during operation, the end cam follower bearing may be associated with a table motion counterweight. Alternatively, the drive shaft may be associated with a crank shaft supported at the end distal to the motor by a pillow block bearing. The crankshaft may be of a known design, i.e. similar to those known for use with single cylinder gas engines, having counterbalancing weights in two different planes to allow precise balancing of the table mass. A connecting rod attached at one end to the offset throw of the crankshaft, and at the other end to the tray pillow block bearing as described above, in order to drive sample tray motion in substantially the same manner as in the previously described embodiment.

As in the vibrator-driven aspect of the invention, the tray further comprises at least one clamp adapted to secure the lid to the tray. The clamps may be configured in the same manner as with the vibrator-driven table. Similarly, the sample tray and lid assembly is also configured to hold multiple samples.

Figure 6:
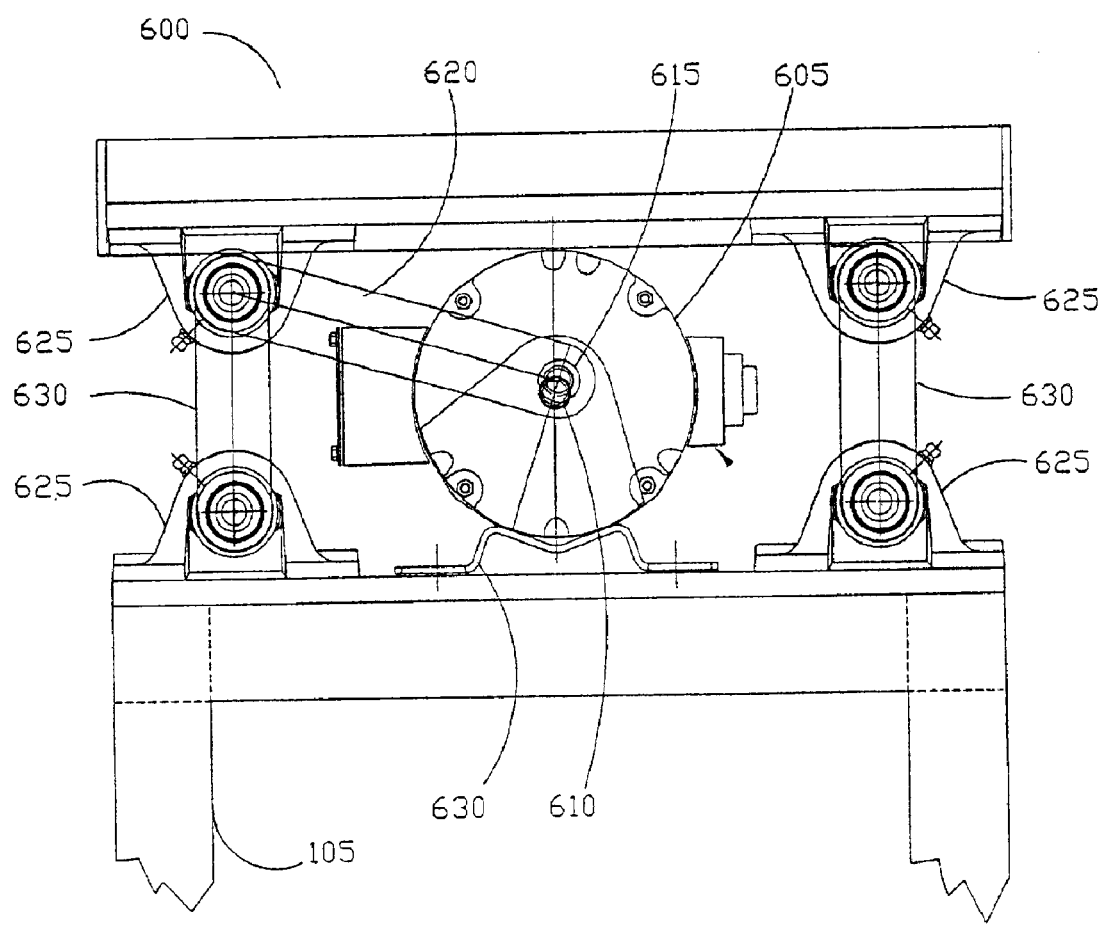
FIG. 6 is a side view of an alternative embodiment of the grinding table described herein.
Figure 7:
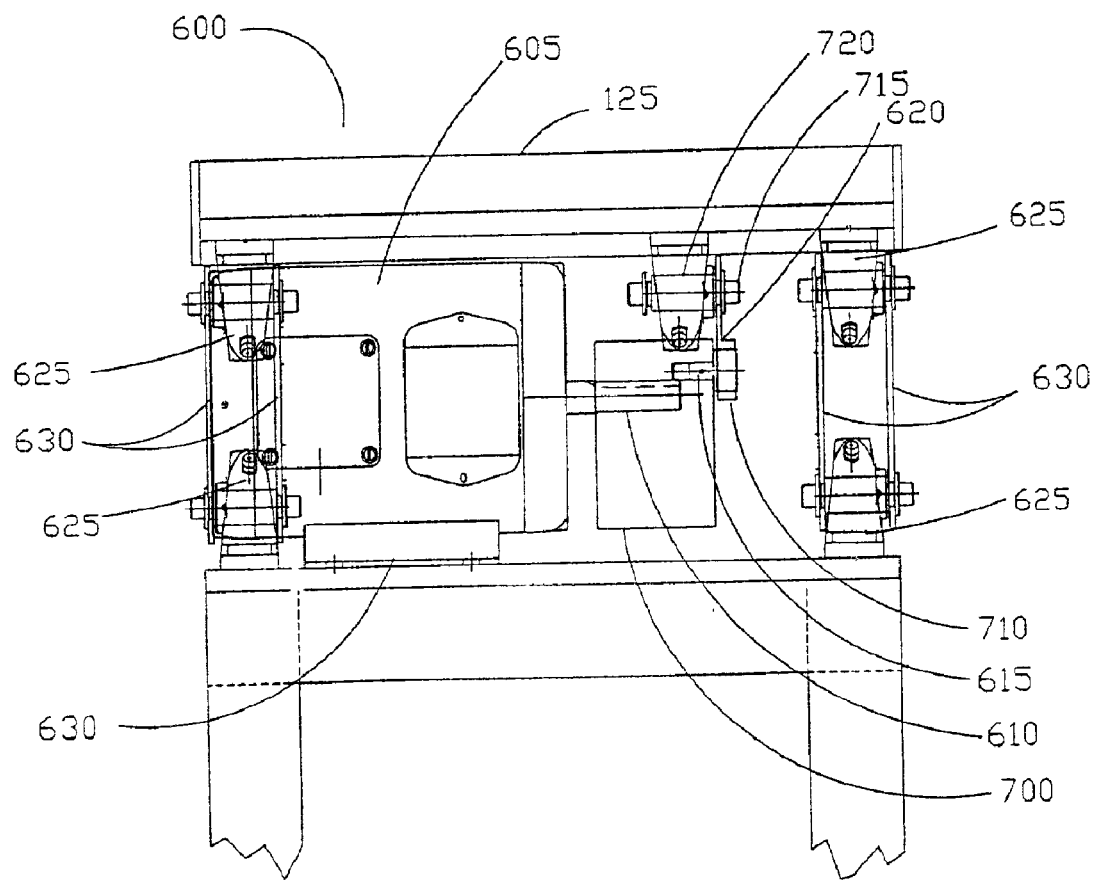
FIG. 7 is a side view of the grinding table viewed as from the left of the perspective shown in FIG. 6.

Referring to FIGS. 6 and 7, a motor-driven, counterbalanced, mechanically linked grinding table is shown. FIG. 6 shows a side-view of the grinding table 600. Tray 125 is linked to frame 105 via pillow block bearing assemblies 625, located at each corner of the lower surface of tray 125, and at each corresponding corner of the top of frame 105. Corresponding pillow block bearing assemblies 625 are linked to one another via bearing connecting links 630 (also see FIG. 7). Motor 605 is mounted via bracket 630 to frame 105. Drive shaft 610 communicates with end cam follower 615. End cam follower 625 is linked to connecting rod 620 via end cam follower bearing 710 (see FIG. 7).

FIG. 7 shows connecting rod 620 linked to actuator pillow block bearing assembly 720 which is mounted on the bottom surface of tray 125 and positioned proximal to one edge of tray 125 between similarly oriented pillow block bearings 630. FIG. 7 also shows table motion counterweight 700 associated with end cam follower bearing 710. Bearing connector links 630 are also shown connecting pillow block bearing assemblies 600 (two bearing connector links 630 per corresponding pair of tray-associated and frame-associated pillow block bearing assemblies 600).

As will be recognized, the mechanical linkage grinding table described herein moves the sample tray in both the horizontal and vertical axis/direction. The motion is provided and controlled by connecting links 630 and connecting rod 620, as described above. As force is applied in a reciprocating manner through connecting rod 620, tray 125 follows a path of travel determined by a radius defined by connecting links 630. This arrangement provides motion having a horizontal and vertical component to all samples in a uniform fashion across the entire sample array held by tray 125.

Process for Achieving Uniform and Reproducible Pulverization

As noted above, the inventors believe that certain aspects of the motion provided by the grinding tables of the invention is responsible for the uniform and reproducible pulverization of a relatively large number of samples. Ball-milling of friable solids requires a relatively vigorous motion of sample containers. A particular challenge met by the grinding tables described herein is the achievement of intense horizontal and vertical grinding bead motion within a relative large number of sample containers. The horizontal and vertical motion components of the grinding beads are an important aspect of the process described herein.

Accordingly, in a further aspect, the present invention provides a process for achieving uniform and reproducible pulverization of friable solids utilizing a ball-mill type action. The process involves securing from about 1 to about 165 sample containers comprising individual samples and grinding beads in a tray; and moving the tray vigorously such that motion of the tray comprises both a horizontal and vertical component. In one embodiment, at least about 50 sample containers are secured in the tray. In another embodiment, at least about 150 sample containers are secured in the tray. In still another embodiment, about 165 sample containers are secure in the tray.

While specific embodiments have been set forth as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

What is claimed is:

1. A grinding table for pulverizing solid materials, comprising
   a frame comprising vertical and horizontal members;
   a control unit mounted on the frame;
   a vibrator in communication with the control unit;
   a tray mounted on the frame by at least one resilient member, the tray comprising a plurality of sample cells adapted to receive a plurality of sample containers containing sample material and grinding beads, the tray being in mechanical communication with the vibrator; and
   a lid for covering and securing the sample containers, the lid adapted to be secured to the tray, wherein the grinding table is adapted to generate both horizontal and vertical oscillation of the grinding beads in the sample containers.

2. A grinding table as in claim 1, wherein the vertical members of the frame are spaced apart to support the horizontal members, the horizontal members forming a substantially rectangular top portion.

3. A grinding table as in claim 1, wherein the tray is connected to the frame by a plurality of resilient members.

4. A grinding table as in claim 3, wherein the resilient members are coiled springs.

5. A grinding table as in claim 1, wherein the vibrator is a rotary electric vibrator.

6. A grinding table as in claim 1, wherein the vibrator is mounted in contact with a bottom surface of the tray.

7. A grinding table as in claim 1, wherein the control unit is an electrical control unit comprising a start button, a stop button, a speed display, a speed control, a disconnect switch, and a process timer.

8. A grinding table as in claim 1, wherein the tray further comprises at least one clamp adapted to secure the lid to the tray.

9. A grinding table as in claim 1, wherein the plurality of sample cells comprises from about 50 sample cells to about 165 sample cells.

10. A grinding table as in claim 1, wherein the plurality of sample cells comprises at least about 150 sample cells.

11. A grinding table for pulverizing solid materials, comprising
    a frame comprising vertical members spaced apart to support horizontal members, the horizontal members forming a substantially rectangular top portion;
    an electrical control unit mounted on the frame, the electrical control unit comprising a start button, a stop button, a speed display, a speed control, a disconnect switch, and a process timer;
    a rotary electric vibrator in communication with the electrical control unit;
    a substantially rectangular tray mounted on the frame by coiled springs attached at an upper end proximal to corners of the tray and at a lower end to corresponding positions proximal to corners to the rectangular top portion of the frame, the tray comprising a plurality of sample cells adapted to received a plurality of sample containers containing sample material and grinding beads, the tray being in mechanical communication with the rotary electric vibrator so that tray about a vertically disposed axis and a first horizontally disposed axis and the coiled springs allow additional movement about a second horizontally disposed axis perpendicular to the first horizontal axis and additional movement about the vertically disposed axis; and
    a lid for covering and securing the sample containers, the lid adapted to be secured to the tray by a plurality of clamps which are attached substantially at a midpoint of each side of the tray.

12. A grinding table for pulverizing solid materials, comprising
    a frame comprising vertical and horizontal members;
    a control unit mounted on the frame;
    a driver in communication with the control unit;
    a series of mechanical linkages comprising a counterbalanced cam mechanism in communication with the driver;
    a tray mounted on the frame via mechanical linkages, the tray having a plurality of sample cells adapted to received a plurality of sample containers containing a sample and grinding beads, the tray being in mechanical communication with the mechanical linkages which are in communication with the driver so that the driver provides a substantially elliptical movement to the tray about a vertically disposed axis and a first horizontally disposed axis, and the coiled springs allow additional movement about a second horizontally disposed axis perpendicular to the first horizontal axis and additional movement about the vertically disposed axis; and a lid for covering and securing the sample containers, the lid adapted to be secured to the tray, wherein the grinding table is adapted to generate substantially uniform grinding of the samples by the grinding beads in the sample containers held by the tray.

13. A grinding table as in claim 12, wherein the series of mechanical linkages in communication with the driver and the mechanical linkages mounting the tray to the frame are adapted to provide motion to the tray comprising both a horizontal and vertical component.

14. A grinding table as in claim 12, wherein the tray is mounted on the frame via mechanical linkages which further comprise pillow block bearing assemblies mounted in corresponding positions on a bottom surface of the tray and on a top portion of the frame, and wherein each corresponding pair of pillow block bearing assemblies is connected by at least one bearing connecting link.

15. A grinding table as in claim 12, wherein the driver is an electric motor.

16. A grinding table as in claim 15, wherein the electric motor is mounted to the frame.

17. A grinding table as in claim 16, wherein the electric motor comprises a drive shaft which communicates with an end cam follower and an associated bearing assembly linked to a connector rod which is connected at an opposite end to a pillow block bearing assembly mounted on a bottom surface of the tray.

18. A grinding table as in claim 17, wherein the end cam follower bearing is associated with a table motion counterweight.

19. A grinding table as in claim 12, wherein the tray further comprises at least one clamp adapted to secure the lid to the tray.

20. A grinding table as in claim 12, wherein the plurality of sample cells comprises from about 50 sample cells to about 165 sample cells.

21. A grinding table as in claim 12, wherein the plurality of sample cells comprises at least about 150 sample cells.

22. A grinding table as in claim 12, wherein the series of mechanical linkages comprises a crankshaft.

23. A grinding table for pulverizing solid materials, comprising a frame comprising vertical and horizontal members, the horizontal members forming a substantially rectangular top portion;

a tray comprising a plurality of sample cells adapted to receive at least about 50 sample containers containing a sample and grinding beads and a plurality of clamps for attachment of a lid, the tray being mounted on the frame by mechanical linkages comprising pairs of pillow block bearing assemblies mounted on a bottom surface of the tray and in corresponding positions on a top portion of the frame, each corresponding pair of pillow block bearing assemblies being connected by at least one bearing connecting link;

an electric motor mounted on the frame and comprising a drive shaft which communicates with an end cam follower and an associated bearing assembly comprising a table motion counterweight, the end cam bearing being linked to a connector rod which is connected at an opposite end to a pillow block bearing assembly mounted on a bottom surface of the tray; and a lid for covering and securing the sample containers, the lid adapted to be secured to the tray via the plurality of clamps, wherein the grinding table is adapted to generate uniform motion of the grinding beads in the sample containers held by the tray and wherein the series of mechanical linkages in communication with the driver and the mechanical linkages mounting the tray to the frame are adapted to provide motion to the tray having a substantially elliptical movement about a vertically disposed axis and a first horizontally disposed axis, and additional movement about a second horizontally disposed axis perpendicular to the first horizontal axis and additional movement about the vertically disposed axis.

24. A grinding table for pulverizing solid materials, comprising, a table having a plurality of components;

a means for supporting the components of the table;

a means for providing motion to moving parts of the table;

a means for controlling the means for providing motion;

a means for securing from about 50 sample containers to about 150 sample containers, the means for securing in communication with the means for providing motion;

means for connecting the means for securing and the means for supporting;

means for connecting the means for securing and the means for providing motion; and wherein the means for connecting for securing and the means for providing motion is adapted to provide motion comprising both a vertical and horizontal component to the means for securing the sample containers so that the motion is substantially elliptical about a vertically disposed axis and a first horizontally disposed axis, and the motion is additionally about a second horizontally disposed axis perpendicular to the first horizontal axis and additionally about the vertically disposed axis.

* * * * *